United States Patent
Wang et al.

(10) Patent No.: US 7,799,927 B2
(45) Date of Patent: Sep. 21, 2010

(54) INDOLESTYRYL COMPOUND AND HIGH DENSITY RECORDING MEDIA UTILIZING THE SAME

(75) Inventors: Shin-Shin Wang, Hsinchu (TW); Chien-Wen Chen, Pingtung County (TW); Jong-Lieh Yang, Hsinchu (TW); Chii-Chang Lai, Taichung Hsien (TW); Hui-Ping Tsai, Hsinchu (TW); Wen-Ping Chu, Taichung (TW); Wen-Yih Liao, Taichung (TW); Chien-Liang Huang, Taoyuan County (TW); Tzuan-Ren Jeng, Hsinchu (TW); Ching-Yu Hsieh, Hsinchu County (TW); An-Tse Lee, Taipei County (TW)

(73) Assignee: Industrial Technology Research Institute, Hsinchu (TW)

( * ) Notice: Subject to any disclaimer, the term of this patent is extended or adjusted under 35 U.S.C. 154(b) by 652 days.

(21) Appl. No.: 11/410,967

(22) Filed: Apr. 26, 2006

(65) Prior Publication Data

US 2007/0219377 A1    Sep. 20, 2007

(30) Foreign Application Priority Data

Mar. 16, 2006    (TW) .............................. 95108963 A

(51) Int. Cl.
C07D 517/02 (2006.01)
C07D 277/62 (2006.01)
C07D 263/54 (2006.01)
C07D 235/04 (2006.01)
C07D 209/04 (2006.01)

(52) U.S. Cl. ...................... 548/120; 548/121; 548/152; 548/217; 548/302.7; 548/469

(58) Field of Classification Search .................. 548/100
See application file for complete search history.

(56) References Cited

U.S. PATENT DOCUMENTS 6,379,768 B1    4/2002    Saito et al.

2002/0028918 A1    3/2002    Kasada et al.
2002/0034605 A1    3/2002    Matsui et al.
2003/0203148 A1    10/2003    Huang et al.
2005/0244576 A1*    11/2005    Jarvenkyla .................. 427/180

FOREIGN PATENT DOCUMENTS

JP    2002-2117 A    1/2002
TW    593564    6/2004
TW    200512190    4/2005

* cited by examiner

Primary Examiner—Kamal A Saeed
Assistant Examiner—Shawquia Young
(74) Attorney, Agent, or Firm—Birch, Stewart, Kolasch & Birch, LLP

(57) ABSTRACT

An indolestyryl compound. The indolestyryl compound has formula (I):

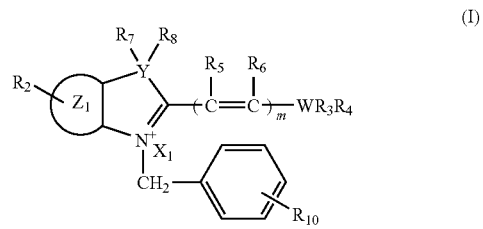

wherein $Z_1$ comprises benzene, naphthalene, or heterocyclic ring containing O, S, or N, $R_2$ comprises H, halogen atoms, $C_{1-5}$ alkyl, nitro, ester, carboxyl, sulfo, sulfonamide, sulfuric ester, amide, $C_{1-3}$ alkoxy, amino, alkylamino, cyano, $C_{1-6}$ alkylsulfonyl, or $C_{2-7}$ alkoxy carbonyl, $R_3$, $R_4$, $R_5$, and $R_6$ comprise H, alkyl, aralkyl, or heterocyclic ring containing O, S, or N, $R_7$ and $R_8$ comprise H or alkyl, $R_{10}$ comprises H, alkyl, halogen atoms, nitro, hydroxyl, amino, ester, or substituted or non-substituted sulfonyl, W comprises carbon or nitrogen, Y comprises carbon, oxygen, sulfur, selenium, —NR, or —C(CH$_3$)$_2$, m is 1~3, and $X_1$ comprises an anionic group or an anionic organometallic complex, wherein $R_3$ and $R_4$ are joined to a nitrogen atom or $R_5$ and $R_6$ are joined together to form a ring, and R bonded to nitrogen is $C_{1-5}$ alkyl.

7 Claims, 2 Drawing Sheets

INDOLESTYRYL COMPOUND AND HIGH DENSITY RECORDING MEDIA UTILIZING THE SAME

BACKGROUND OF THE INVENTION

1. Field of the Invention

The invention relates to an indolestyryl compound, and in particular relates to an indolestyryl compound used in a high density recording medium.

2. Description of the Related Art

With advances in information and multimedia generation, computer, communication, and consumer (3C) electronic products with increased recording density and capacity, microminiaturization, and low cost are demanded. Currently, magnetic recording media are often replaced by high density optical recording media.

Conventional 650 MB CD-R or 4.7 GB DVD-R media are insufficient for 2-hour digital programs, requiring 25-50 GB or more. Blue laser disks with 405 nm read-out wavelength and 25 GB single-layer capacity or more provide a workable option, thus, development of applicable organic dyes is desirable.

BRIEF SUMMARY OF THE INVENTION

The invention provides an indolestyryl compound having formula (I):

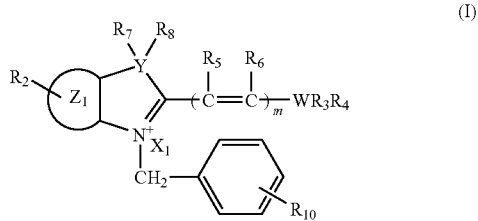

(I)

wherein $Z_1$ comprises benzene, naphthalene, or heterocyclic ring containing O, S, or N, $R_2$ comprises H, halogen atoms, $C_{1-5}$ alkyl, nitro, ester, carboxyl, sulfo, sulfonamide, sulfuric ester, amide, $C_{1-3}$ alkoxy, amino, alkylamino, cyano, $C_{1-6}$ alkylsulfonyl, or $C_{2-7}$ alkoxy carbonyl, $R_3$, $R_4$, $R_5$, and $R_6$ comprise H, alkyl, aralkyl, or heterocyclic ring containing O, S, or N, $R_7$ and $R_8$ comprise H or alkyl, $R_{10}$ comprises H; alkyl, halogen atoms, nitro, hydroxyl, amino, ester, or substituted or non-substituted sulfonyl, W comprises carbon or nitrogen, Y comprises carbon, oxygen, sulfur, selenium, —NR, or —C(CH$_3$)$_2$, m is 1~3, and $X_1$ comprises an anionic group or an anionic organometallic complex, wherein $R_3$ and $R_4$ are joined to a nitrogen atom or $R_5$ and $R_6$ are joined together to form a ring, and R bonded to nitrogen is $C_{1-5}$ alkyl.

The invention also provides a high density recording medium comprising a first substrate, a recording layer formed thereon comprising the disclosed indolestyryl compound, a reflective layer formed on the recording layer, and a second substrate formed on the reflective layer.

The invention further provides a high density recording medium comprising a first substrate, a reflective layer formed thereon, a recording layer formed on the reflective layer comprising the disclosed indolestyryl compound, and a protective layer formed on the recording layer.

A detailed description is given in the following embodiments with reference to the accompanying drawings.

BRIEF DESCRIPTION OF THE DRAWINGS

The invention can be more fully understood by reading the subsequent detailed description and examples with references made to the accompanying drawing, wherein.

DETAILED DESCRIPTION OF THE INVENTION

Figure 1:
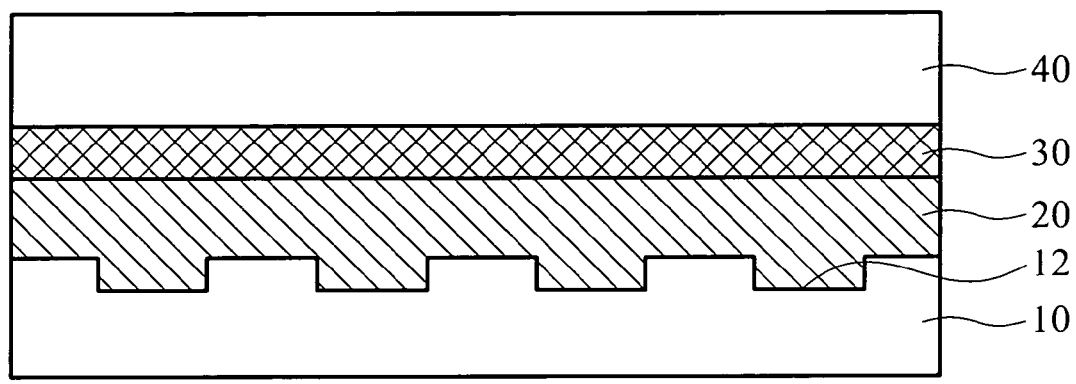
FIG. 1 is a cross section of a high density recording medium of the invention.

The following description is of the best-contemplated mode of carrying out the invention. This description is made for the purpose of illustrating the general principles of the invention and should not be taken in a limiting sense. The scope of the invention is best determined by reference to the appended claims.

The invention provides an indolestyryl compound having formula (I):

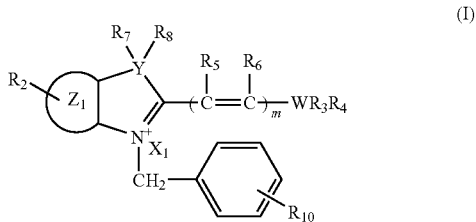

(I)

In formula (I), $Z_1$ may comprise benzene, naphthalene, or heterocyclic ring containing O, S, or N. The heterocyclic ring containing O, S, or N may comprise furan, pyrazine, pyrrole, pyrazole, pyridazine, pyridine, pyridone, pyrimidine, thiazole, thiophene, quinine, and isoquinine.

$R_2$ may comprise H, halogen atoms, $C_{1-5}$ alkyl, nitro, ester, carboxyl, sulfo, sulfonamide, sulfuric ester, amide, $C_{1-3}$ alkoxy, amino, alkylamino, cyano, $C_{1-6}$ alkylsulfonyl, or $C_{2-7}$ alkoxy carbonyl.

$R_3$, $R_4$, $R_5$, and $R_6$ may comprise H, alkyl, aralkyl, or heterocyclic ring containing O, S, or N. $R_3$ and $R_4$ may be joined to a W atom or $R_5$ and $R_6$ may be joined together to form a ring. Substituted groups in $R_3$, $R_4$, $R_5$, and $R_6$ may comprise H, halogen atoms, alkyl, alkyl halide, nitro, cyano, hydroxyl, carboxyl, ester, sulfo, sulfuric ester, or sulfoamide.

$R_7$ and $R_8$ may comprise H or alkyl. $R_{10}$ may comprise H, alkyl, halogen atoms, nitro, hydroxyl, amino, ester, or substituted or non-substituted sulfonyl. W may be carbon or nitrogen atom. Y may be carbon, oxygen, sulfur, selenium, —NR, or —C(CH$_3$)$_2$, wherein R is $C_{1-5}$ alkyl. m is 1~3 and $X_1$ may be anionic groups or anionic organometallic complexes. The anionic groups may comprise halogen atoms, ClO$_4^-$, BF$_4^-$, PF$_6^-$, BPh$_4^-$, SbF$_6^-$, tetracyano p-quinodimethane (TCNQ$^-$), tetracyano ethylene (TCNE$^-$), or benzene sulfonate. The anionic organometallic complexes may comprise

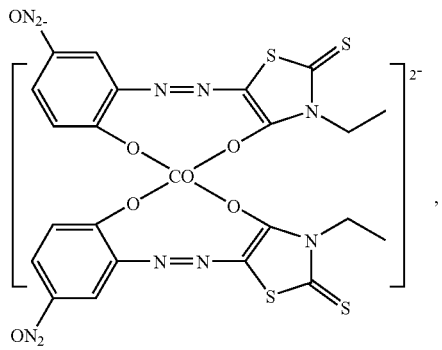

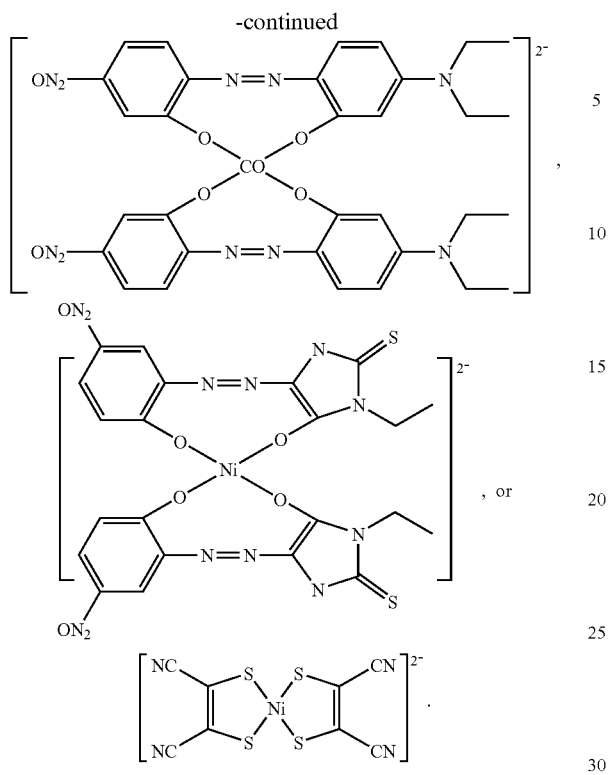

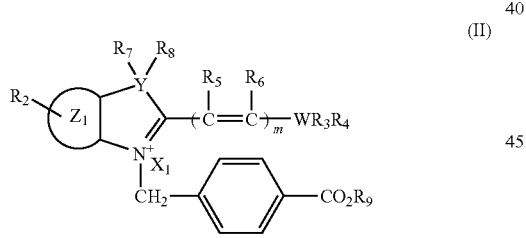

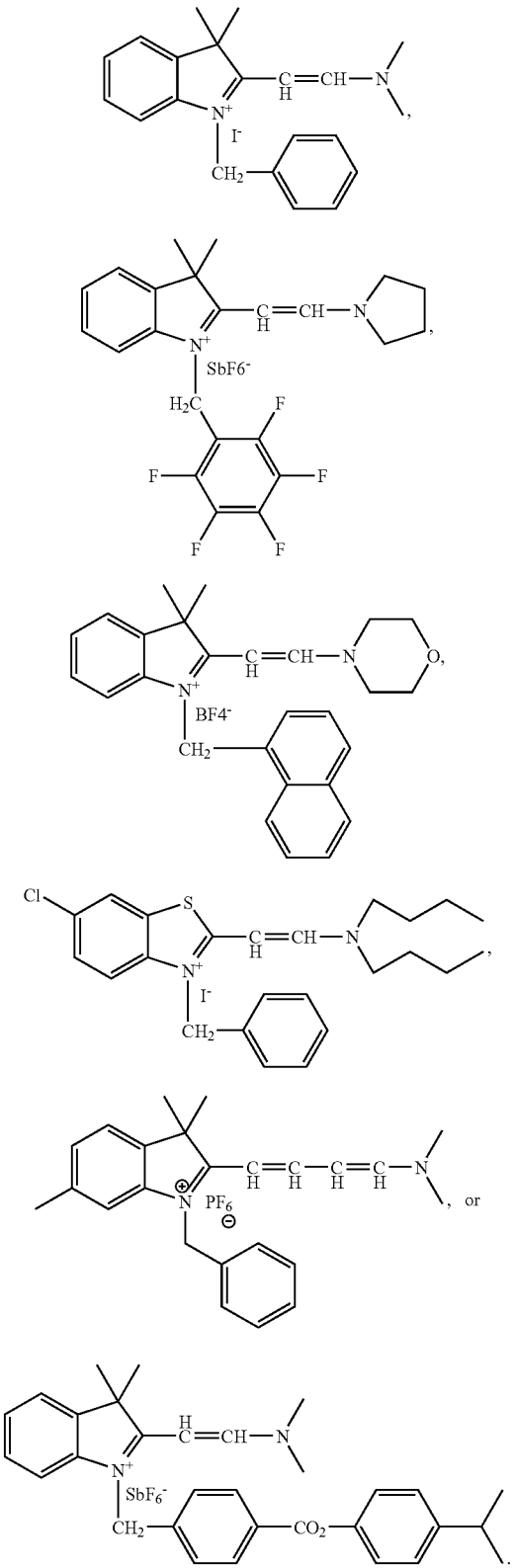

The disclosed indolestyryl compound has an absorbing wavelength of about 300~500 nm, an absorbing coefficient ($\epsilon$) exceeding $1\times10^4$, and solubility exceeding 1% in organic solvent such as $C_{1-6}$ alcohol, $C_{1-6}$ ketone, $C_{1-6}$ ether, dibutyl ether (DBE), halide, or amide.

The disclosed indolestyryl compound has formula (II):

In formula (II), $Z_1$ may comprise benzene, naphthalene, or heterocyclic ring containing O, S, or N.

$R_2$ may comprise H, halogen atoms, $C_{1-5}$ alkyl, nitro, ester, carboxyl, sulfo, sulfonamide, sulfuric ester, amide, $C_{1-3}$ alkoxy, amino, alkylamino, cyano, $C_{1-6}$ alkylsulfonyl, or $C_{2-7}$ alkoxy carbonyl.

$R_3$, $R_4$, $R_5$, and $R_6$ may comprise H, alkyl, aralkyl, or heterocyclic ring containing O, S, or N.

$R_7$ and $R_8$ may comprise H or alkyl. $R_9$ may comprise H, alkyl, or substituted or non-substituted benzene or naphthalene. W may be carbon or nitrogen. Y may be carbon, oxygen, sulfur, selenium, —NR, or —C(CH$_3$)$_2$, wherein R is $C_{1-5}$ alkyl. m is 1~3 and $X_1$ may be anionic groups or anionic organometallic complexes.

The indolestyryl compound provided by the invention comprises

The indolestyryl compound of formula (I) is prepared as follows. A compound such as

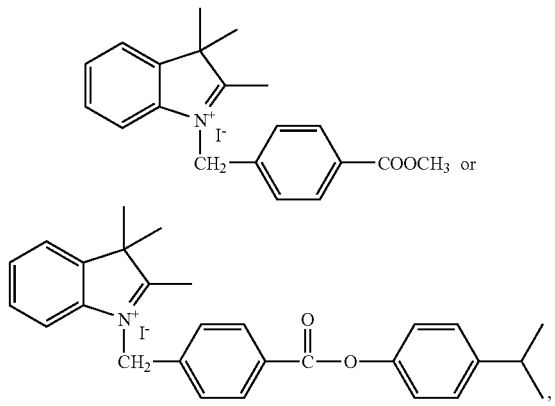

solvent such as ethanol or methanol, and an aldehyde compound such as N,N,-dimethylformaldehyde (DMF) are added to a flask and reacted for 20~24 hours. An indolestyryl compound is prepared after extracting solvent. The indolestyryl compound, solvent such as methanol or ethanol, and a metal salt are then added to a flask and reacted overnight. The metal salt may comprise Li, Na, or K salt such as $NaSbF_6$, $NaClO_4$, or $NaPF_6$. After cooling to room temperature and filtration, an indolestyryl compound is produced.

The invention also provides a high density recording medium comprising a first substrate, a recording layer formed thereon comprising the disclosed indolestyryl compound, a reflective layer formed on the recording layer, and a second substrate formed on the reflective layer.

The invention further provides a high density recording medium comprising a first substrate, a reflective layer formed thereon, a recording layer formed on the reflective layer comprising the disclosed indolestyryl compound, and a protective layer formed on the recording layer.

The first substrate is a transparent substrate having trenches. The second substrate is a transparent substrate without trenches. The first and second substrates may comprise polyester, polycarbonate ester, polyolefin, or metallocene based cyclic olefin copolymer. The recording layer has a thickness of about 50~300 nm and further comprises cyanine dye, azo metal chelate compounds, or oxonol compounds. The indolestyryl compound and cyanine dye, azo metal chelate compounds, or oxonol compounds have a weight ratio of about 1:99~99:1. The reflective layer may comprise Au, Ag, Al, Si, Cu, Cr, Ti, or alloys thereof.

The high density recording medium has a reflectance of about 40~60%. The high density recording medium may be a high density Disk-Recordable (HD DVD-R and BD-R).

A method of fabricating a high density recording medium is provided. A first substrate is provided and a solution containing an indolestyryl compound and solvent prepared simultaneously. The solvent may comprise $C_{1-6}$ alcohol, $C_{1-6}$ ketone, $C_{1-6}$ ether, dibutyl ether (DBE), halide, or amide. The $C_{1-6}$ alcohol may be methanol, ethanol, isopropanol, diacetone alcohol (DAA), 2,2,3,3-tetrafluoropropanol (TFP), trichloroethanol, 2-chloroethanol, octafluoropentanol, or hexafluorobutanol. The $C_{1-6}$ ketone may be acetone, methyl isobutyl ketone (MIBK), methyl ethyl ketone (MEK), or 3-hydroxy-3-methyl-2-butanone. The halide may be chloroform, dichloromethane, or 1-chlorobutane. The amide may be dimethyl formamide (DMF), dimethyl acetamide (DMA), or methyl cyclohexane (MCH). The solution is then coated on the first substrate and dried to form a recording layer, utilizing spin coating, vacuum deposition, spray coating, immersion coating, stick coating, fluid coating, print coating, or tape coating, preferably spin coating. Next, a reflective layer is sputtered on the recording layer. Finally, a second substrate is bonded to the reflective layer to form a high density recording medium utilizing spin coating, printing coating, thermal melted-glue, or double-faced tape bonding. A protective layer may be coated on the reflective layer before the second substrate is bonded.

Another method of fabricating a high density recording medium is also provided. A first substrate is provided. Next, a reflective layer is sputtered on the substrate. A solution containing an indolestyryl compound and solvent is prepared simultaneously. The solvent may comprise $C_{1-6}$ alcohol, $C_{1-6}$ ketone, $C_{1-6}$ ether, dibutyl ether (DBE), halide, or amide. The $C_{1-6}$ alcohol may be methanol, ethanol, isopropanol, diacetone alcohol (DAA), 2,2,3,3-tetrafluoropropanol (TFP), trichloroethanol, 2-chloroethanol, octafluoropentanol, or hexafluorobutanol. The $C_{1-6}$ ketone may be acetone, methyl isobutyl ketone (MIBK), methyl ethyl ketone (MEK), or 3-hydroxy-3-methyl-2-butanone. The halide may be chloroform, dichloromethane, or 1-chlorobutane. The amide may be dimethyl formamide (DMF), dimethyl acetamide (DMA), or methyl cyclohexane (MCH). The solution is then coated on the reflective layer and dried to form a recording layer, utilizing spin coating, vacuum deposition, spray coating, immersion coating, stick coating, fluid coating, print coating, or tape coating, preferably spin coating. Finally, a protective layer is coated on the recording layer to form a high density recording medium.

EXAMPLE 1

Preparation of Compound 1

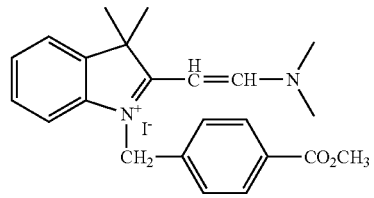

4.53 g

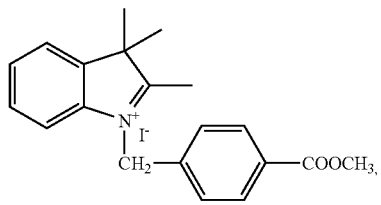

2.92 g N,N-dimethylformaldehyde, and 50 ml methanol were added to a flask and reacted overnight. After cooling to room temperature and filtration, 2.55 g brown compound 1 was prepared with yield of 52%. Compound 1 had a maximum absorbing wavelength of 371 nm in methanol.

EXAMPLE 2

Preparation of Compound 2

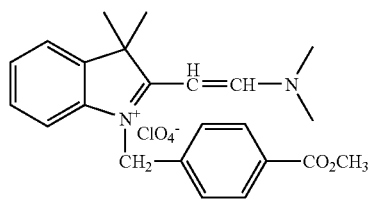

4.9 g compound 1, 2.44 g NaClO$_4$, and 50 ml methanol were added to a flask and reacted overnight. After cooling to room temperature and filtration, 4.0 g brown compound 2 was prepared with yield of 89%. Compound 2 had a maximum absorbing wavelength of 371 nm in methanol.

EXAMPLE 3

Preparation of Compound 3

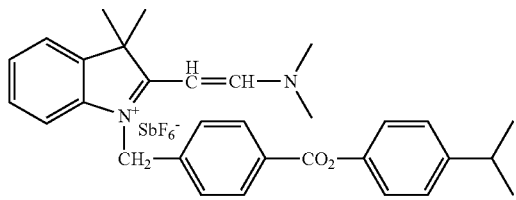

10.79 g

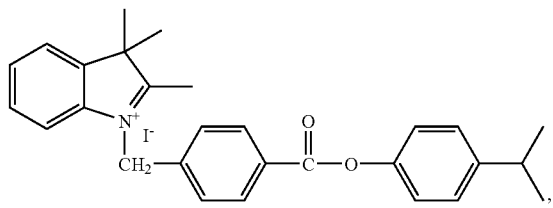

5.85 g N,N-dimethylformaldehyde, and 50 ml methanol were added to a flask and reacted overnight. After cooling to room temperature and filtration, 10.22 g brown solid compound was prepared. 5.94 g brown solid compound, 5.16 g NaSbF$_6$, and 50 ml methanol were then added to a flask and reacted overnight. After cooling to room temperature and filtration, 6.4 g red-brown compound 3 was prepared with yield of 91%. Compound 3 had a maximum absorbing wavelength of 373 nm in methanol.

In accordance with Examples 1 to 3 and Table 1, the photoelectrical properties (for example maximum absorbing wavelength, absorbing coefficient, degradation temperature and eflectance) of compounds 1 to 3 are different due to various anionic ions or R$_{10}$ thereof. Thus, in Formula (I), the variables Z$_1$, R$_2$, R$_3$, R$_4$, R$_{10}$, m and X$_1$ have effects on the photoelectrical

EXAMPLE 4

Preparation of Compound 4

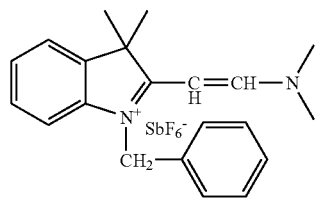

2 g

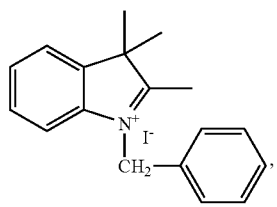

0.43 g N,N-dimethylformaldehyde, and 50 ml methanol were added to a flask and reacted overnight. After cooling to room temperature and filtration, 1.2 g brown solid compound was prepared. 1 g brown solid compound, 0.66 g NaSbF$_6$, and 50 ml methanol were then added to a flask and reacted overnight. After cooling to room temperature and filtration, 0.45 g red-brown compound 4 was prepared with yield of 36%. Compound 4 had a maximum absorbing wavelength of 371 nm in methanol.

Maximum absorbing wavelengths ($\lambda_{max}$), absorbing coefficient ($\epsilon$) degradation temperature (° C.), and reflectance (%) of compounds 1~3 are shown in Table 1.

TABLE 1

| Compounds | Maximum absorbing wavelengths (nm) | | Absorbing coefficient ($\times 10^4$) | Degradation temperature (° C.) | Reflectance (%) |
|---|---|---|---|---|---|
| | methanol | film | | | |
| 1 | 371 | 378 | 7.64 | 182.6 | 41 |
| 2 | 371 | 378 | 7.53 | 190.2 | 43 |
| 3 | 373 | 379 | 7.98 | 192.1 | 42 |

EXAMPLE 5

Fabrication of High Density Recording Medium

Figure 2:
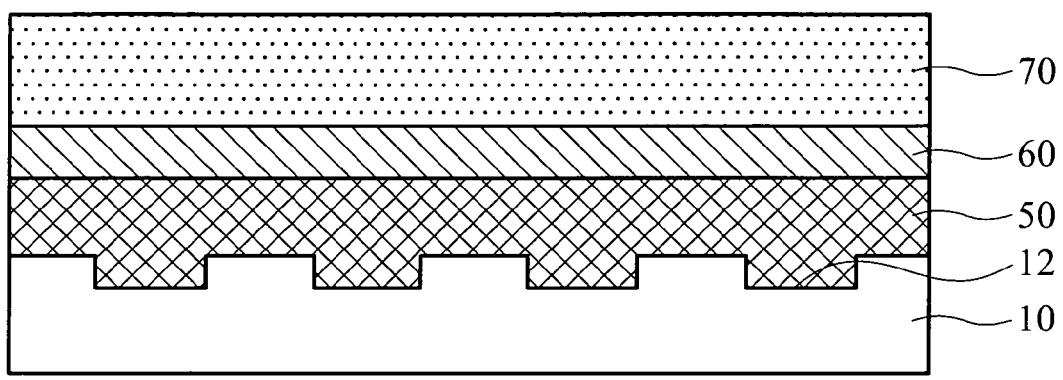
FIG. 2 is a cross section of another high density recording medium of the invention.

Referring to FIGS. 1 and 2, two methods of fabricating high density recording mediums are disclosed according to the following examples. In FIG. 1, a polycarbonate ester first substrate 10 at a diameter of 120 mm and a thickness of 0.6 mm having trenches 12 at a depth of 122 nm and a width of 400 nm was provided. A solution (1.5 wt %) containing a compound 2 and 2,2,3,3-tetrafluoropropanol (TFP) was prepared simultaneously. Next, the solution was coated on the first substrate 10 by spin coating and dried at 80° C. for 5 min to form a recording layer 20. An Ag layer was then sputtered on the recording layer 20 to form a reflective layer 30 at a thickness of 150 nm. Finally, a second substrate 40 was bonded to the reflective layer 30 to form a blue-laser high density recording medium. A UV resin was coated on the reflective layer 30 to form a protective layer of about 10 μm (not shown) before the second substrate 40 was bonded. The disk had a reflectance of about 43% under 405 nm.

In FIG. 2, a polycarbonate ester first substrate 10 at a diameter of 120 mm and a thickness of 1.1 mm having trenches 12 at a depth of 122 nm and a width of 400 nm was provided. Next, an Ag layer was sputtered on the first substrate 10 to form a reflective layer 50 at a thickness of 150 nm. A solution (1.5 wt %) containing a compound 3 and 2,2,3,3-tetrafluoropropanol (TFP) was prepared simultaneously. Next, the solution was coated on the reflective layer 50 by spin coating and dried at 80° C. for 5 min to form a recording layer 60. Finally, a UV resin was coated on the recording layer 60 to form a protective layer 70 of about 10 μm. The disk had a reflectance of about 42% under 405 nm.

While the invention has been described by way of example and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. An indolestyryl compound of formula (I):

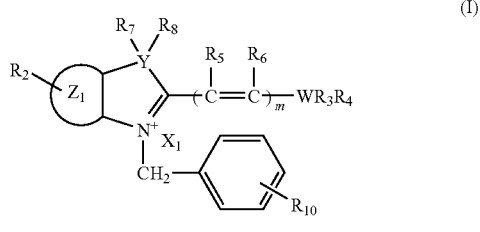

(I)

wherein $Z_1$ is benzene or naphthalene, $R_2$ is H, halogen, $C_{1-5}$ alkyl, nitro, ester, carboxyl, sulfo, sulfonamide, sulfuric ester, amide, $C_{1-3}$ alkoxy, amino, alkylamino, cyano, $C_{1-6}$ alkylsulfonyl, or a $C_{2-7}$ alkoxy carbonyl, $R_3$, $R_4$, $R_5$, and $R_6$ are each independently selected from the group consisting of H, alkyl, aralkyl, and a heterocyclic ring containing O, S, or N, $R_7$ and $R_8$ are each independently selected from the group consisting of H and an alkyl, $R_{10}$ is H, alkyl, halogen, nitro, hydroxyl, amino, ester, or a substituted or non-substituted sulfonyl, W is carbon or nitrogen, Y is carbon, oxygen, sulfur, selenium, —NR, or —C(CH$_3$)$_2$, m is 1-3, and $X_1$ is an anionic group or an anionic organometallic complex, wherein $R_3$ and $R_4$ are joined to a nitrogen atom or $R_5$ and $R_6$ are joined together to form a ring, and R bonded to nitrogen is $C_{1-5}$ alkyl.

2. The indolestyryl compound as claimed in claim 1, wherein substituted groups in $R_3$, $R_4$, $R_5$, and $R_6$ are each independently selected from the group consisting of H, halogen, alkyl, alkyl halide, nitro, cyano, hydroxyl, carboxyl, ester, sulfo, sulfuric ester, and sulfoamide.

3. The indolestyryl compound as claimed in claim 1, wherein $X_1$ is a halogen, $ClO_4^-$, $BF_4^-$, $PF_6^-$, $BPh_4^-$, $SbF_6^-$, tetracyano p-quinodimethane (TCNQ$^-$), tetracyano ethylene (TCNE$^-$), benzene sulfonate,

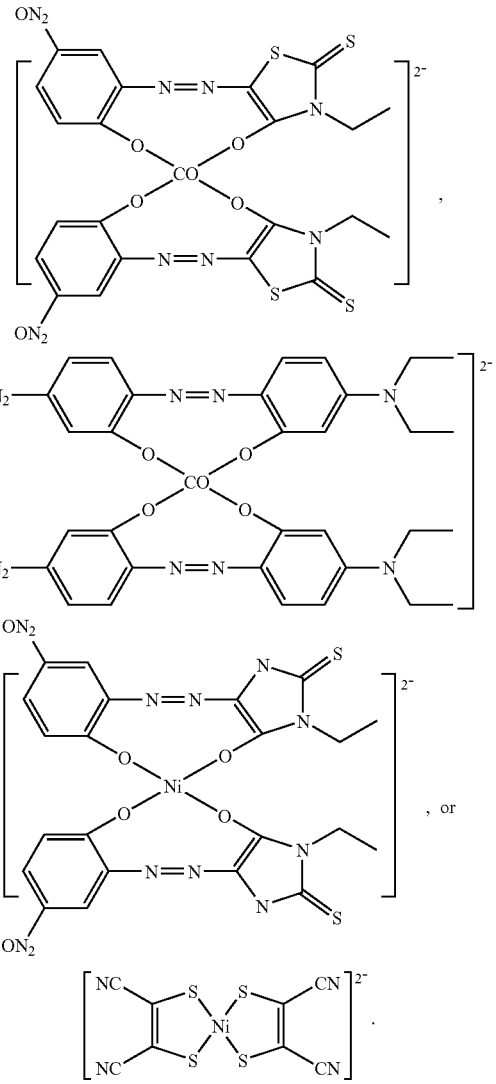

4. The indolestyryl compound as claimed in claim 1, wherein the compound of formula (II):

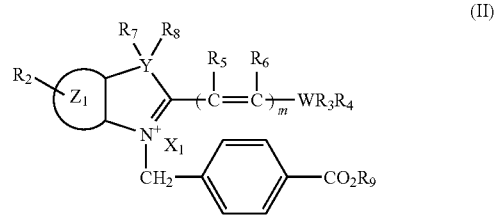

(II)

wherein $Z_1$ is benzene or naphthalene, $R_2$ is H, halogen, $C_{1-5}$ alkyl, nitro, ester, carboxyl, sulfo, sulfonamide, sulfuric ester, amide, $C_{1-3}$ alkoxy, amino, alkylamino, cyano, $C_{1-6}$ alkylsulfonyl, or a $C_{2-7}$ alkoxy carbonyl, $R_3$, $R_4$, $R_5$, and $R_6$ are each independently selected from the group consisting of H, alkyl, aralkyl, and a heterocyclic ring containing O, S, or N, $R_7$ and $R_8$ are each independently selected from the group consisting of H and an alkyl, $R_9$ is H, alkyl, or a substituted or non-substituted benzene or naphthalene, W is carbon or nitrogen, Y is carbon, oxygen, sulfur, selenium, —NR, or —C(CH$_3$)$_2$, m is 1-3, and X$_1$ is an anionic group or an anionic organometallic complex, wherein R bonded to nitrogen is C$_{1-5}$ alkyl.

5. The indolestyryl compound as claimed in claim 1, wherein the compound has an absorbing wavelength of about 300-500 nm.

6. The indolestyryl compound as claimed in claim 1, wherein the compound has solubility exceeding 1% in organic solvent.

7. The indolestyryl compound as claimed in claim 6, wherein the organic solvent is a C$_{1-6}$ alcohol, C$_{1-6}$ ketone, C$_{1-6}$ ether, dibutyl ether (DBE), halide, or an amide.

* * * * *